United States Patent [19]

Mahendroo

[11] 4,257,877

[45] Mar. 24, 1981

[54] SELECTIVE HYDROGENATION PROCESS

[75] Inventor: Rajinder K. Mahendroo, Fords, N.J.

[73] Assignee: Engelhard Minerals & Chemicals Corporation, Iselin, N.J.

[21] Appl. No.: 754,991

[22] Filed: Dec. 28, 1976

[51] Int. Cl.³ .................... C07C 15/02; C10G 45/32; C10G 45/44
[52] U.S. Cl. .................................. 208/144; 208/143; 585/258; 585/259
[58] Field of Search .............................. 208/143, 144; 260/677 H, 668 R; 585/258, 259

[56] References Cited

U.S. PATENT DOCUMENTS

| | | | |
|---|---|---|---|
| 3,268,608 | 8/1966 | DeRosset | 260/668 R |
| 3,539,500 | 11/1970 | Brooks et al. | 208/143 |
| 3,769,358 | 10/1973 | Neta et al. | 260/677 H |

Primary Examiner—Herbert Levine

[57] ABSTRACT

In a process for the selective hydrogenation of unsaturated hydrocarbon components of a feedstock, the feedstock is initially passed over a hydrogenation catalyst in the absence of hydrogen to increase hydrogenation selectivity of the catalyst, after which the amount of hydrogen required is then passed over the catalyst along with the feedstock to carry out the desired hydrogenation reaction.

11 Claims, No Drawings

SELECTIVE HYDROGENATION PROCESS

BACKGROUND OF THE INVENTION

The present invention relates to the hydrogenation of unsaturated hydrocarbon compounds, and more particularly to the selective hydrogenation of one or more unsaturated compounds, or unsaturated portions of compounds contained in a feedstock.

The use of selective hydrogenation of hydrocarbon compounds to prepare particular products and/or to confer desirable characteristics to various feedstocks is known throughout the oil and chemical industry. For example, selective hydrogenation is utilized to selectively remove olefins and diolefins from aromatic feedstocks to prevent the polymerization of these compounds, and hence avoid contamination of the products of later treatment of the feedstock. An example of this process is the hydrogenation of conjugated aliphatic or cyclic diolefins in naphtha streams that are blended into gasoline products or further processed for extraction of aromatic compounds.

Selective hydrogenation is also utilized to preferentially hydrogenate a portion or portions of hydrocarbon compounds while leaving unaltered other unsaturated portions of the same compound. For example, in the preparation of cumene (isopropylbenzene), alpha-methylstyrene is processed so as to hydrogenate the unsaturated aliphatic branch thereof without hydrogenating the aromatic benzene ring. Additionally, in those cumene production processes wherein the alpha-methylstyrene feedstock contains either naturally occurring or recycled cumene, ring saturation must obviously especially be avoided.

Catalysts and process conditions have been developed in this field to achieve the preferential hydrogenation required by the foregoing processes. Typically, catalysts containing supported noble metals such as platinum, palladium or ruthenium are utilized.

While the foregoing catalysts are generally effective in achieving an acceptable degree of hydrogenation specificity, improvement in this area is consistently sought. For example, it has been proposed to add certain organic nitrogen compounds to the feedstock in order to improve the selectivity of processes designed to produce cyclohexenes and substituted cyclohexenes by hydrogenation; see U.S. Pat. No. 3,793,383 to Johnson, et al.

Of particular concern in this area is the observation that catalyst selectivity in hydrogenation processes is poor when virgin or freshly regenerated catalysts are utilized, the selectivity gradually increasing as the catalyst ages onstream. Thus, undesired aromatic ring hydrogenation occurs in the early stages of the process, leading to product losses, the need for appropriate separatory equipment, and possible temperature runaways due to the high activity of the catalyst. In the belief that the poor selectivity of fresh catalysts is attributable to rapid temperature rises at the start-up of the hydrogenation process, it has been proposed to place limits on the temperature and amount of hydrogen present at the start-up of the process; see U.S. Pat. No. 3,769,358 to Neta, et al. There is a need, however, for further improvement in obtaining greater catalytic hydrogenation selectivity.

It is accordingly an object of this invention to develop an improved process for the selective hydrogenation of unsaturated hydrocarbon compounds.

A particular object of this invention is to improve the hydrogenation selectivity of hydrogenation catalysts, especially virgin or freshly regenerated hydrogenation catalysts.

In accordance with this invention, the selectivity of hydrogenation catalysts, particularly virgin or freshly regenerated catalysts, is increased by a process comprising contacting a feedstock with a hydrogenation catalyst in the absence of hydrogen for a period of time sufficient to increase the hydrogenation selectivity of the catalyst, and thereafter contacting the hydrogenation catalyst with the feedstock and hydrogen to carry out the desired hydrogenation reaction.

The feedstock employed may be comprised of (a) at least one unsaturated compound for which hydrogenation is intended in the process and at least one unsaturated compound which is intended to remain unsaturated, or (b) a compound having a first unsaturated portion which is intended to be hydrogenated in the process, and a second unsaturated portion which is intended to remain unsaturated, or (c) a mixture of (b) and an unsaturated compound which is intended to remain unsaturated.

Exemplary feedstocks are respectively, (a) a mixture of olefins or diolefins in an aromatic feedstock such as naphtha wherein it is desired to hydrogenate the olefins without causing hydrogenation of the aromatic ring structure; (b) alpha-methylstyrene, wherein it is desired to hydrogenate the aliphatic portion thereof without causing hydrogenation of the aromatic ring; and (c) a mixture of alpha-methylstyrene and cumene, wherein the aromatic ring of each compound is intended to remain unsaturated while hydrogenation of the unsaturated aliphatic portion of the alpha-methylstyrene is effected.

According to a specific embodiment of the present invention, alpha-methylstyrene is converted to cumene by contacting a feedstock containing alpha-methylstyrene with a noble metal catalyst in the absence of hydrogen and thereafter introducing hydrogen along with the feedstock to selectively hydrogenate the aliphatic portion of the alpha-methylstyrene without causing hydrogenation of the aromatic ring.

The duration of time during which the feedstock is contacted with the hydrogenation catalyst in the absence of hydrogen is not believed of critical importance, it being noted that catalyst selectivity is improved after short periods of such pretreatment, and continues to improve in a fairly regular manner as the length of pretreatment is extended. As is apparent to those skilled in this art, practical considerations such as economics may dictate the extent of pretreatment, e.g., the degree of improvement in selectivity achieved for each increase in the duration of pretreatment may at some point become so small as to not warrant any longer periods of pretreatment. Additionally, the extent of pretreatment should not be so long as to adversely shorten the catalyst cycle length by reducing catalyst activity.

Once the desired degree of pretreatment, i.e., the contact of the feedstock with the catalyst in the absence of hydrogen, is completed, hydrogenation proceeds according to well-known procedures. The conditions at which such selective hydrogenation is conducted will, of course, vary depending upon the feedstock to be treated and the hydrogenation desired, but typical processes utilize temperatures in the range of from about 60° C. to about 200° C., pressures in the range of from about 80 psig, to about 1500 psig, and liquid hourly space velocities in the range of from about 0.25 to about 40. The feedstock to be hydrogenated is maintained principally in the liquid phase and the molar ratio of hydrogen to the unsaturated hydrocarbon to be hydrogenated in the feedstock may be in the range of from about 1:1 to about 5:1.

While the foregoing conditions may similarly be utilized during the pretreatment in the absence of hydrogen, successful operation has been achieved utilizing pretreatment temperatures of 40° C. and atmospheric pressure, while maintaining a primarily liquid phase.

The catalysts utilized in the foregoing processes may be any of the well-known hydrogenation catalysts, generally comprised of a supported metal having a large surface area. Suitable metals include particularly the noble metals such as ruthenium, rhodium, palladium and platinum. Suitable supports include natural or treated clays such as kaolin or bentonite, siliceous materials, magnesium oxide, silica gel, alumina gel, zeolites, and activated carbon and in suitable form, such as pellets, spheres, extrudates, and the like. Activated aluminas such as alpha-alumina, eta-alumina and gamma-alumina are especially useful supports. Preferred catalysts comprise platinum or palladium on alumina supports. When utilizing these or other noble metals on a support, the noble metal will typically be present in the range of from about 0.01% to about 5% by weight of the catalytic composition, and preferably in the range of from about 0.2% to about 2.0% by weight.

While it is not desired to be bound by the following, it is presently theorized that the results of the present invention are attributable to the fact that the increase of hydrogenation selectivity with catalyst age is the result of the formation during hydrogenation of polymerization products such as oligomers of the unsaturated components of the feed and the deposit of such products on the catalyst surface. The effect appears to be an actual modification of the catalyst by virtue of the blinding of certain active sites of the catalyst which otherwise promote undesired ring hydrogenation. The present invention hastens the production of these products by initially excluding hydrogen from the reaction and only thereafter commencing with the desired hydrogenation over the pre-treated or "pre-aged" catalyst.

Such pretreatment should be carried out until the catalyst has reached the desired selectivity, since an extended period may reduce the useful on-stream time and require more frequent regeneration of the catalyst. Where the feedstock is highly unsaturated, it is often desirable to utilize an inert diluent, for example recycled hydrogenated product, in conjunction with the pretreatment feed.

The following examples are provided to illustrate the process of the present invention.

EXAMPLE I

A feedstock of the following composition
Alpha-methylstyrene: 19.8% by weight
Hydroxyacetone: 280 p.p.m.
Benzofuran: 110 p.p.m.
Cumene: Balance
was passed over a catalyst composition comprised of 0.3% palladium on ⅛ inch diameter cylindrical alumina pellets at atmospheric pressure and a liquid weight hourly space velocity 2.0 (lbs. feed/lb. catalyst/hr) for 12 hours. During the first six hours the pretreatment was conducted at substantially adiabatic conditions with a stepwise increase of the inlet feed temperatures from 40° C. to 80° C. over this period. The reaction was then continued isothermally at 80° C. for an additional six hours.

Following this pretreatment, hydrogenation was commenced at a pressure of 100 psig., a temperature of 80° C., liquid hourly space velocity of 2.0, and a hydrogen to alpha-methylstyrene mole ratio of 4:1.

Table I summarizes the results of this hydrogenation process. The effectiveness of the catalyst selectivity is monitored by measurement of the production of isopropyl cyclohexane which indicates that hydrogenation of the aromatic ring structure has occurred. Despite the decrease in hydrogenation of alpha-methylstyrene to isopropyl cyclohexane, the hydrogenation to cumene remains high, indicating that selectivity of the catalyst is improving.

TABLE I

| Hours on Stream (After Pre-Treatment) | IPCH[1] in Product p.p.m. (wt) | AMS[2] in Product (wt. percent) |
|---|---|---|
| 4.2 | 361 | .1 |
| 5.6 | 367 | .07 |
| 6.1 | 353 | .06 |
| 6.6 | 321 | .06 |
| 7.1 | 279 | .06 |
| 7.6 | 239 | .06 |
| 8.1 | 243 | .05 |
| 8.6 | 206 | .05 |
| 9.1 | 240 | .04 |
| 25.3 | 66 | .04 |
| 26.3 | 32 | .03 |

[1]Isopropyl cyclohexane
[2]alpha-methylstyrene

EXAMPLE II

Utilizing a feedstock nearly identical with that processed in Example I (21% alpha-methylstyrene in cumene), hydrogenation without first pretreating the catalyst was conducted at the same hydrogenating conditions and with the same catalyst type (freshly prepared) employed in Example I except that the hydrogen to alpha-methylstyrene mole ratio was 3.5. The results are summarized in Table II.

TABLE II

| Hours on Stream | IPCH in Product p.p.m. wt. | AMS in Product wt. percent |
|---|---|---|
| .8 | 1820 | .07 |
| 1.3 | 1560 | .03 |
| 1.8 | 1450 | .02 |
| 2.3 | 1280 | .02 |
| 2.8 | 1260 | .02 |
| 3.8 | 1240 | .01 |
| 20.6 | 750 | .02 |
| 23.3 | 660 | <.01 |
| 25.8 | 610 | <.01 |
| 28.3 | 550 | <.01 |
| 44.6 | 130 | <.01 |
| 45.6 | 110 | <.01 |

It will be noted comparing Tables I and II that the pretreatment according to the invention has reduced the production of isopropyl cyclohexane substantially while not affecting the hydrogenation of alpha-methylstyrene to cumene.

EXAMPLE III

Utilizing the same feedstock as described in Example I, alpha-methylstyrene was converted to cumene by passing the feedstock over a freshly prepared catalyst of the composition described in Example I, without pretreating the catalyst, at 400 psig., 103° C., a liquid weight hourly space velocity of 1.72, and a hydrogen to alpha-methylstyrene mole ratio of 4.5. The results are summarized in Table III.

TABLE III

| Hours on Stream | IPCH in Product p.p.m wt. | AMS in Product wt. percent |
|---|---|---|
| 0.7 | 82200 | .73 |
| 1.2 | 52400 | .20 |
| 2.2 | 37700 | .099 |
| 5.0 | 31100 | .045 |
| 9.0 | 24400 | .024 |
| 22.5 | 9600 | .009 |
| 45.0 | 2600 | <.01 |

The production of isopropyl cyclohexane under the more severe hydrogenation conditions of Example III is much greater than in Example II. Although the data show that IPCH concentration is declining with time a longer period would be required to reach the level of Examples I and II. Thus increasing the severity of the hydrogenation conditions does not provide the improvement of catalyst selectivity accomplished by the pretreatment of the invention.

When calculated in terms of the length of time at hydrogenation conditions for the IPCH level to fall below 100 p.p.m., the process of Example I took approximately eighteen hours while the process of Example II took approximately 50–60 hours, and that of Example III 70–80 hours, thus demonstrating the effectiveness of pretreating the catalyst according to the invention.

While the comparative data presented is with particular reference to the selective hydrogenation of alpha-methylstyrene, the process of the present invention has applicability to other processes wherein selective hydrogenation is required, particularly where it is desired to suppress the rate of aromatic ring hydrogenation.

What is claimed is:

1. A process for improving selective hydrogenation of unsaturated hydrocarbon compounds comprising initially contacting hydrogenation catalyst at a pressure in the range of from about atmospheric to about 1500 psig. in the absence of hydrogen at a temperature in the range of from about 40° C.-200° C. with a feedstock maintained in the liquid phase, said feedstock comprising (a) at least one unsaturated compound for which hydrogenation is intended in the process and at least one unsaturated compound which is intended to remain unsaturated, or (b) a compound having a first unsaturated portion which is intended to be hydrogenated in the process, and a second unsaturated portion which is intended to remain unsaturated, or (c) a mixture of (b) and an unsaturated compound which is intended to remain unsaturated, to improve the hydrogen selectivity of the catalyst, and thereafter contacting said catalyst with a mixture of said feedstock and hydrogen at conditions which effect hydrogenation of the unsaturated compound or portion thereof intended to be hydrogenated.

2. The process of claim 1 wherein said unsaturated compound or portion thereof which is intended to remain unsaturated comprises an aromatic moiety.

3. The process of claim 2 wherein said feedstock is naphtha comprising one or more unsaturated aliphatic compounds for which hydrogenation is intended.

4. The process of claim 2 wherein said feedstock comprises a compound containing an aromatic ring portion for which hydrogenation is not intended, and an unsaturated aliphatic portion for which hydrogenation is intended.

5. The process of claim 1 wherein said feedstock comprises alpha-methylstyrene.

6. The process of claim 2 wherein said feedstock comprises a mixture of alpha-methylstyrene and cumene.

7. The process of claim 1 wherein said hydrogenation conditions comprise temperature in the range of from about 60° C. to about 200° C., pressure in the range of from about 80 psig. to about 1500 psig. and a mole ratio of hydrogen to unsaturated hydrocarbon to be hydrogenated in the range of from about 1:1 to about 5:1.

8. The process of claim 7 wherein said hydrogenation catalyst comprises a noble metal selected from the group consisting of palladium, platinum and mixtures thereof.

9. A process for the production of cumene comprising passing a feedstock comprised of alpha-methylstyrene in the liquid phase over a hydrogenation catalyst in the absence of hydrogen at a temperature of from about 40° C. to about 100° C., a pressure of from about atmospheric to about 500 psig. and a liquid weight hourly space velocity in the range of from about 0.5 to about 10 for a period of time sufficient to improve the hydrogenation selectivity of said catalyst; and thereafter contacting said catalyst with a mixture of said feedstock and hydrogen at a mole ratio of hydrogen to alpha-methylstyrene in the range of from about 1:1 to about 5:1, said alpha-methylstyrene being present in more than trace quantities in said feedstock.

10. The process of claim 9 wherein said hydrogenation catalyst is selected from the group consisting of freshly prepared and freshly regenerated supported noble metals.

11. The process of claim 1 wherein virgin or regenerated noble metal catalyst is contacted with feedstock at a temperature of from about 40° C.-80° C.

* * * * *